United States Patent [19]

Christensen

[11] Patent Number: Plant 6,758

[45] Date of Patent: Apr. 25, 1989

[54] HYBRID TEA ROSE PLANT CV. AROTIGY

[75] Inventor: Jack E. Christensen, Ontario, Calif.

[73] Assignee: Bear Creek Gardens, Inc., Medford, Oreg.

[21] Appl. No.: 126,876

[22] Filed: Nov. 30, 1987

[51] Int. Cl.[4] ..... A01H 5/00

[52] U.S. Cl. ..... Plt./11

[58] Field of Search ..... Plt./11, 22

*Primary Examiner*—Robert E. Bagwill

*Attorney, Agent, or Firm*—Majestic, Parsons, Siebert & Hsue

[57] ABSTRACT

This invention relates to a new and distinct variety of hybrid tea rose plant cv. Arotigy, identified by its clusters of bright yellow flowers, the petal edges of which are bordered with red.

1 Drawing Sheet

The present invention relates to a new and distinct variety (cv. Arotigy) of rose plant of the hybrid tea class. The plant is an average height, hardy outdoor seedling of the bush type, cultivated for garden decoration. It was first originated by Jack E. Christensen in Ontario, Calif., U.S.A. under conditions of careful control and observation, and has as its seed parent the floribunda rose, Gingersnap (U.S. Plant Pat. No. 4,330), and as its pollen parent, the grandiflora rose Macbern (U.S. Plant Pat. No. 4,063).

The new rose cv. Arotigy is particularly distinguishable from other commercialized rose cultivars by the following combination of characteristics: its bright yellow blossoms having a red border on the petal margins, the red border developing in the absence of strong sunlight; the light and spicy fragrance of its blossoms; and the clustering of its blooms, 2 to 4 flowers per stem, essentially as described and illustrated herein.

Arotigy holds its distinguishing characteristics through succeeding propagations by cuttings, budding and in vitro culture.

The new variety cv. Arotigy may be distinguished from its seed parent, Gingersnap, by the following combination of characteristics: Whereas Gingersnap is a floribunda rose, Arotigy is a hybrid tea rose. The flower color of Arotigy is a bright yellow with a red border on the petal margins whereas the flower color of Gingersnap is a pure orange.

The new variety may be distinguished from its pollen parent, Macbern, by the following combination of characteristics: Whereas the flower color of Macbern is a medium yellow, the flower color of Arotigy is a bright yellow with a red border on the petal margins. Macbern rose plants grow significantly larger than plants of Arotigy. Whereas the foliage of Macbern is very glossy, the foliage of Arotigy is non-glossy.

The accompanying drawing illustrates the new variety in color as grown in Somis, Calif., and shows the flowering thereof from bud to full bloom.

The descriptive matter which follows pertains to roses of the new variety grown in the outdoors in Somis, Calif., and is believed generally to apply to similar conditions elsewhere. Plants and flowers of the new variety grown in other locations may vary in slight detail according to the climatic, soil and cultural conditions under which the variety is grown.

Throughout this specification, color names beginning with a small letter signify that the name of that color as used in common speech is aptly descriptive. Color names beginning with a capital letter designate values based upon the R.H.S. Colour Chart of The Royal Horticultural Society of London, England.

FLOWER

The new variety sometimes bears its flowers singly, usually two to three to a stem in irregular clusters. Flowers are borne on weak to average strength stems that are average to long in length for the class. In the greenhouse and outdoors, the plant blooms in moderate abundance and intermittently during the growing season. Blooms have a light and spicy fragrance.

BUD

The peduncle is of average length for the class, of slender to average caliper, and slightly bending. The peduncle is almost smooth with some stipitate glands. Bud color is near Green 143B.

Before the calyx breaks, the bud is small in size for the class, ovoid in form with a conspicuous neck. There are few stipitate glands on the surface of the bud, and slender, serrate, bristle-like foliaceous parts extending beyond the tip of the bud and equal to three quarters or more of its length.

As the calyx breaks, sepals are near Green 143B and near Yellow 4B between the sepals, tinted with near Red 39A.

The inner surface of the sepals bears a fine wooly tomentum. Sepal margins are lined with stipitate glands and hairs.

As the first petal opens, buds are small in size for the class, short and pointed to ovoid in shape. Color of the outside and inside of the bud petals is an orange-red-yellow blend, the yellow (near Yellow 5A) is the predominant color, and is overlaid with a bright red-orange (near Red 43A) color, which is more concentrated along the petal margin, and which extends ⅓ the way down the inside and outside petal surface.

The bud opens up well and is not prevented from opening by cold, hot, wet or dry weather.

BLOOM

The size of the bloom when fully open is small to average for the class, about 2½ to about 3 inches in diameter. Petalage is double, averaging from about 28 to 30 petals arranged regularly, plus 2 to 3 petaloids. At one-half open, blooms are somewhat high-centered in form, with spiraled cupped petals. Petal edges are reflexed outward. When fully open, blooms are cupped with petals similarly cupped, the petal edges moderately reflexed outward. Inside petals may be irregularly arranged.

The petals are heavy in substance, thick in texture and slightly satiny on the inside and outside surface. Outside petals are nearly round in shape with tips usually bearing one to two notches. Intermediate petals are nearly round to broadly obovate with rounded tips usually bearing one to two notches. Inside petals are nearly oval with tips usually bearing one to two notches.

The following paragraph describes the color values observed in a newly opened flower from a plant of the new variety grown outdoors in Somis, Calif. in October of 1987.

The outside surface of the outside petals is near Yellow 8A in color, and bordered with near Red 43A at the petal margins which bleeds down the petal surface about ¼ inch from the margin. The inside surface of the outside and inner petals is near yellow 9A in color, bordered at the petal margins with near Red 43A. The outside surface of the intermediate and inner petals is near Yellow 9A in color and bordered with near Red 43A at the petal margins which bleeds down the petal surface about ¼ inch from the margin.

Petal colors may be modified by being washed or tinted with other colors.

The following paragraph describes the color values observed in a flower open for three days outdoors from a plant of the new variety in October, 1987 at Somis, Calif.

The color of the outside surface of both the outside and inside petals is pale yellow, near Yellow 10D in color, bordered at the petal margins with a pale red, near Red 39B which bleeds down the petal surface about ¼ inch from the margin. The inside surface of the outside petals is a pale yellow-green, near Yellow 1C, bordered at the petal margins with a pale red, near Red 39B, which bleeds down the petal surface about ¼ inch from the margin. The inside surface of the inside petals is approximately the same as the outside surface of the inside petal except the yellow color is less pale, near Yellow 2B.

The general color effect of newly opened flowers is a bright yellow with a red border along the petal margins. Flowers open for three days are a paler yellow with a pale red border along the petal margin.

Petals usually drop off cleanly and are not particularly affected by hot, wet or dry weather. Flowers on garden plants last from 3 to 4 days in the month of October. Cut flowers from rose plants grown outdoors last from 2 to 3 days in October when kept at living room temperatures.

REPRODUCTIVE ORGANS

Stamens are few to average in number and arranged irregularly about the pistils; a few may also be mixed with petaloids or tucked in with the calyx. Filaments are short in length and few are without anthers. Anthers are of average size and open all at once. Mature anthers are near Yellow-Orange 20A in color; immature anthers are near Yellow-Orange 19A in color. Pollen is produced in moderate quantities and is near Yellow-Orange 20B in color.

Pistils are few to average in number for the class (about 27). Styles are uneven, of thin caliper and of average length. Styles are loosely bunched. Stigma color is near Yellow-Orange 19B on the surface and pink-red, near Red 39B, just below the surface. Some ovaries are enclosed in the calyx and some protrude therefrom.

The variety appears to be highly female sterile as the flower and peduncle die before the hip is formed.

The recurved sepals fall soon.

FOLIAGE

The compound leaves comprise 3 to 5 leaflets. Leaves are borne in average quantities, are average in size for the class, of moderate to heavy weight and are non-glossy. Leaflets are oval in shape, with acute apices; their bases are round and margins are dentate.

The color of the mature upper leaf surface is near Green 139A; the mature lower leaf surface is near Green 137D. New growth is near Greyed-Purple 183B in color; the under surface of young leaves is near Red-Purple 58A.

The rachis is of average size. Its upper side is grooved with few stipitate glands on the edges. The underside is moderately smooth with few stipitate glands.

Stipules are average in length for the class, of average width, and have moderately short points, slightly recurved toward the stem.

Plants of the new variety are, on the average, more resistant to mildew, rust and blackspot than other cultivars now in commerce when grown under comparable conditions at Somis, Calif.

GROWTH

Plants of the new variety are average in height, bushy and compact in habit. Plant growth is vigorous. Canes are of average caliper for the class. The main stems are Green 137D in color. They bear few to several large thorns which are moderately short for the class and almost straight. Large thorns are near Yellow-Green 154C in color. The thorn base is moderately short and narrow. There are few small prickles, near Greyed-Orange 176C in color and no hairs.

Branches are between near Green 143B and Green 143C in color; they bear no large thorns, no small prickles and no hairs.

New shoots are near Yellow-Green 146C in color. New shoots bear no large thorns, no small prickles and no hairs.

I claim:

1. A new and distinct variety of hybrid tea rose plant cv. Arotigy, and the parts thereof, being particularly characterized by its bright yellow blossoms having a red border on the petal margins, the red border developing in the absence of strong sunlight; the light and spicy fragrance of its blossoms; and the clustering of its blooms, two to four flowers per stem, essentially as described and illustrated herein.

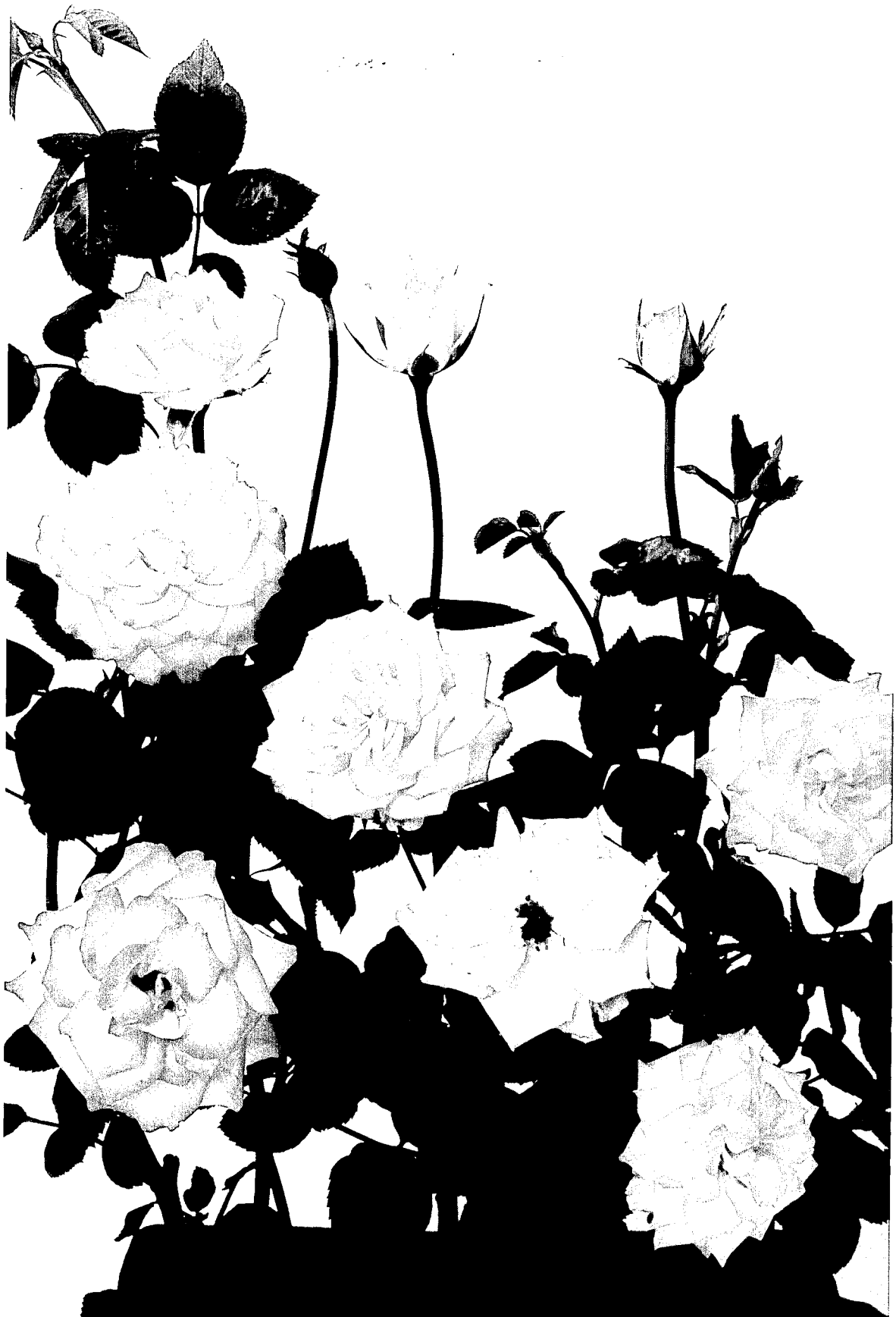

* * * * *